United States Patent [19]
Ginosar et al.

[11] Patent Number: 6,103,948
[45] Date of Patent: Aug. 15, 2000

[54] SOLID CATALYZED ISOPARAFFIN ALKYLATION AT SUPERCRITICAL FLUID AND NEAR-SUPERCRITICAL FLUID CONDITIONS

[75] Inventors: Daniel M. Ginosar; Robert V. Fox; Peter C. Kong, all of Idaho Falls, Id.

[73] Assignee: Bechtel BWXT Idaho, LLC, Idaho Falls, Id.

[21] Appl. No.: 09/219,560

[22] Filed: Dec. 23, 1998

Related U.S. Application Data

[60] Provisional application No. 60/068,842, Dec. 24, 1997.

[51] Int. Cl.$^7$ ..................................................... C07C 2/58
[52] U.S. Cl. ........................... 585/721; 585/722; 585/726; 585/730
[58] Field of Search ................................... 585/721, 722, 585/726, 730

[56] References Cited

U.S. PATENT DOCUMENTS

| | | | |
|---|---|---|---|
| 3,852,371 | 12/1974 | Kemp | 260/683.47 |
| 3,919,343 | 11/1975 | Sobel et al. | 260/683.48 |
| 3,979,476 | 9/1976 | Kemp | 260/683.47 |
| 4,404,418 | 9/1983 | Hutson, Jr. et al. | 585/710 |
| 4,605,811 | 8/1986 | Tiltscher et al. | 585/670 |
| 4,695,665 | 9/1987 | De Graff | 585/450 |
| 4,721,826 | 1/1988 | Tiltscher et al. | 585/670 |
| 4,956,518 | 9/1990 | Child et al. | 585/467 |
| 5,157,196 | 10/1992 | Crossland et al. | 585/726 |
| 5,157,197 | 10/1992 | Cooper et al. | 585/720 |
| 5,292,981 | 3/1994 | Huanag et al. | 585/726 |
| 5,304,698 | 4/1994 | Husain | 585/722 |
| 5,310,713 | 5/1994 | Kojima et al. | 585/719 |
| 5,336,833 | 8/1994 | Joly et al. | 585/722 |
| 5,345,028 | 9/1994 | Alerasool | 585/730 |
| 5,489,732 | 2/1996 | Zhang et al. | 585/731 |
| 5,491,277 | 2/1996 | Stine et al. | 585/722 |
| 5,523,503 | 6/1996 | Funk et al. | 585/467 |
| 5,725,756 | 3/1998 | Subramaniam et al. | 208/48 R |
| 5,907,075 | 5/1999 | Subramaniam et al. | 585/721 |

OTHER PUBLICATIONS

Encyclopedia of Chemical Technology, Alkylation, Kirkothmer, 4$^{th}$ Edition, vol. 2, pp. 84–113.

*Primary Examiner*—Marian C. Knode
*Assistant Examiner*—Thuan D. Dang
*Attorney, Agent, or Firm*—Thorpe North & Western

[57] ABSTRACT

This invention relates to an improved method for the alkylation reaction of isoparaffins with olefins over solid catalysts including contacting a mixture of an isoparaffin, an olefin and a phase-modifying material with a solid acid catalyst member under alkylation conversion conditions at either supercritical fluid, or near-supercritical fluid conditions, at a temperature and a pressure relative to the critical temperature($T_c$) and the critical pressure($P_c$) of the reaction mixture. The phase-modifying phase-modifying material is employed to promote the reaction's achievement of either a supercritical fluid state or a near-supercritical state while simultaneously allowing for decreased reaction temperature and longer catalyst life.

20 Claims, No Drawings

SOLID CATALYZED ISOPARAFFIN ALKYLATION AT SUPERCRITICAL FLUID AND NEAR-SUPERCRITICAL FLUID CONDITIONS

RELATED APPLICATION

This application claims priority from provisional application Ser. No. 60/068,842 filed Dec. 24, 1997.

CONTRACTUAL ORIGIN OF THE INVENTION

The United States has rights in this invention pursuant to Contract No. DE-AC07-94ID13223 between the U.S. Department of Energy and Lockheed Martin Id. Technologies Company.

BACKGROUND OF THE INVENTION

This invention is concerned with a method for causing the isoparaffin-olefin alkylation reaction to occur in either a supercritical fluid or near-supercritical fluid phase over a solid catalyst at temperatures that are substantially lower than analogous supercritical fluid reactions previously reported for the reactants involved.

Alkylation is a reaction wherein an alkyl group is added to an organic molecule. Thus an isoparaffin can be reacted with an olefin to provide an isoparaffin of higher molecular weight. Industrially, the concept depends on the reaction of a $C_2$ to $C_5$ olefin with a $C_4$ to $C_8$ isoparaffin in the presence of an acidic catalyst producing a so-called alkylate. That alkylate is a valuable blending component in the manufacture of gasolines not only to increase its octane rating but also to increase its sensitivity to octane-enhancing additives.

The United States petroleum refining industry production of motor fuel alkylate was 425,700,000 barrels in 1996; with an anticipated growth of 25% over the next 5 years. The world wide motor fuel alkylate production was 812,500,000 barrels in 1996. (Michelle Williamson, "WORLDWIDE REFINING," Oil & Gas Journal, Special issue, 47–90, Dec. 18, 1995). The refining industry currently uses concentrated liquid acids, such as hydrofluoric acid and sulfuric acid, to catalyze the alkylation of aromatics and isoparaffins with olefins for the production of chemical commodities, intermediates, and gasoline blend stocks.

Paraffin alkylation, as discussed here, refers to the addition reaction of an isoparaffin and an olefin. The desired product is a higher molecular weight paraffin that exhibits a greater degree of branching. The principal industrial application of paraffin alkylation is in the production of premium-quality fuels for spark-ignition engines. Originally developed in the late 1930s to meet the fuel requirements of high performance aviation engines, alkylation is now primarily used to provide high octane blending components for automotive fuels. Future gasoline specifications will continue to require the clean burning characteristics and the low emissions typical of the product of paraffin alkylation.

Although alkylation of paraffins can be carried out thermally, catalytic alkylation is the basis of processes in commercial use. Early studies of catalytic alkylation led to the formulation of a proposed mechanism based on a chain of ionic reactions. In practice, however, the paraffin alkylation reaction is a complex reaction that cannot be explained solely by the chain mechanism. Historically, the catalysts used in the industrial paraffin alkylation reaction are strong liquid acids, either sulfuric acid or hydrofluoric acid. Other strong acids have been shown to be capable of promoting alkylation in the laboratory, but have not been used commercially.

Industrial alkylation processes have historically used a hydrofluoric or sulfuric acid catalysts under relatively low temperature conditions. The sulfuric acid alkylation reaction is particularly sensitive to temperature, with low temperatures being used to minimize the side reaction of olefin polymerization. Acid strength in those liquid acid catalyzed alkylation processes is preferably maintained at 88 to 94 weight percent acid by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal problems. Indeed, the toxic nature of hydrofluoric acid has earned it a place on the "ultra hazardous" chemicals list of the EPA. Moreover, the waste sludge produced by either the sulfuric or hydrofluoric acid catalyzed reactions is classified as a hazardous waste and, therefore, is under the stringent controls and regulations of RCRA and CERCLA regulation regimes. The additional expense that such regulated waste management can cost a manufacturer is significant. Research efforts have therefore been directed to developing alkylation catalysts that are as effective as sulfuric or hydrofluoric acids but lack many of the problems associated with those two acids. For a general discussion of acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation see 1 Handbook of Petroleum Refining Processes 23–28 (R. A. Meyers, ed., 1986).

With the increasing demands for octane and the increasing environmental concerns, it has been desirable to develop an alkylate process using safer, more environmentally acceptable catalyst systems. Specifically, it is desirable to provide an industrially viable alternative to the currently used hydrofluoric and sulfuric acid catalyzed alkylation processes. Consequently, substantial efforts have been directed to developing a viable isoparaffin-olefin alkylation process that avoids the environmental and safety problems associated with sulfuric and hydrofluoric acid alkylation systems while retaining the alkylate quality and reliability characteristic of those well-known processes. Research efforts have been directed toward solid as well as liquid alkylation catalyst systems, as reflected in the following references.

U.S. Pat. No. 5,304,698 (hereinafter, "the '698 patent") delineates the three requirements for the alkylation reaction to occur. The reaction must have feedstocks, a suitable catalyst for promoting the reaction, and reaction conditions that promote and sustain the reaction. The general method taught for olefin conversion in the catalytic alkylation of an olefin with an isoparaffin comprises contacting an olefin-containing feed with an isoparaffin-containing feed with a microporous zeolite material. Such zeolite-containing catalysts useful in the process disclosed in the '698 patent include ZSM-4, ZSM-12, ZSM-20, ZSM-35, ZSM-48, ZSM-50, MCM-22, PSH-3, TMA offretite, TEA mordenite, clinoptilolite, mordentite, REY, and zeolite Beta. Further teaching regarding those solid catalysts and their formation can be found in U.S. Pat. Nos. 4,439,409; 3,832,449; 3,972,983 (ZSM-20); 4,016,245 (ZSM-35); 4,397,827 (ZSM-48); 4,640,849 (ZSM-50); 3,308,069 (Beta); and 4,439,409 (PSH-3). The '698 patent further teaches that the group of useful catalysts includes porous crystalline solids and layered materials. The non-zeolitic inorganic oxide of the solid catalyst may be selected from the group of diverse inorganic oxides, such as alumina, zirconium dioxide, chromia, zinc oxide, magnesia, calcium oxide, silica-alumina, silica-magnesia, silica-alumina-magnesia, and silica-alumina-zirconia, as well as the naturally occurring inorganic oxides of various states of purity such as bauxite, clay and diatomaceous earth.

Feedstocks useful in practicing the invention disclosed in the '698 patent include at least one isoparaffin and at least one olefin. The isoparaffin contains from about 4 to about 8 carbon atoms. The olefin component of the feedstock includes at least one olefin having from 2 to 12 carbon atoms.

The reaction conditions disclosed in the '698 patent include temperatures that are at least equal to the critical temperature ($T_c$) of the principal component of the feed and pressures at least equal to the critical pressure ($P_c$) of the principal component of the feed. The term "principal component", as used in the '698 patent, is defined as the component of highest concentration in the feedstock. Specifically, in a preferred embodiment of the '698 patent, the fresh crystalline microporous material contacts the mixed isoparaffin-olefin feed under process conditions that are at least equal to the critical temperature and pressure of the principal component of the feed. The alkylation process disclosed in the '698 patent is suitably conducted at temperatures from about 135° C. up to about 371° C., preferably from about 149° C. to about 316° C. The '698 patent also specifies that the operating temperature must be at least equal to the critical temperature of the principal component in the feed; while simultaneously the pressure must be maintained at least equal to the critical pressure of the principal component in the feed. Finally, the '698 patent teaches the use of conditions under which the principal reaction component, being in a supercritical fluid state, prolongs the useful catalytic life of the crystalline microporous material through physical/chemical mechanisms and properties attributed to the supercritical phase of matter.

U.S. Pat. No. 5,345,028 (hereinafter, "the '028 patent") discloses several methods for the preparation and use of solid catalysts in the olefin isoparaffin alkalation reaction. The '028 patent also discloses three useful methods for the synthesis of solid catalysts of the type used in the present invention. The first disclosed method involves the formation of a sulfated Ni—Ti composition through the addition of $NiCl_2$ to a solution of $TiCl_4$ The resultant Ni—Ti composition is sulfated through the addition of sulfuric acid, and the resultant product is dried and activated according to methods well known in the art. An additional method involves the addition of $Ti(OH)_4$ to $Ni(NO_3)_2$ in an aqueous environment. Upon the complete dissolution of the $NiCl_2$ the composition is dried and activated according to methods well known in the art. The final method of catalyst formation disclosed in the '028 patent involves the addition of freshly prepared $TiO_2$ to an aqueous solution of $Ni(NO_3)_2$. The mixture is stirred, isolated, dried and activated according to methods well known in the art.

The two-part articles "Modern Alkylation", by Lyle F. Albright, published in the Nov. 12 and 26, 1990, issues of the Oil and Gas Journal summarizes the present sulfuric acid and hydrogen fluoride acid alkylation technology.

Thus, while it would be desirable to substitute a solid alkylation catalyst for the liquid catalysts described above, solid catalysts have not proven in the past to be a commercially viable alternative to liquid acid catalysts due to problems with catalyst longevity and alkylate product quality. Additionally, where some success involving the use of solid alkylation catalysts has been published, the reaction conditions require operating at relatively high temperatures. Notably those temperatures are required to be at or above the critical point of the reaction mixture. As previously reported, catalyst deactivation is attenuated and catalyst life is increased when reaction conditions are at or above the critical point of the reaction mixture. However, at those higher temperatures undesirable side reactions, including product isomerization, product cracking, olefin oligomerization and coking, predominate over the desired alkylation reaction, significantly reducing product quality and high octane product yield.

BRIEF SUMMARY OF THE INVENTION

It is an object of this invention to provide a method whereby an industrially useful alkylation reaction can occur under conditions such that the reaction mixture is in either a supercritical or a near-supercritical fluid phase at temperatures lower than those previously available for supercritical fluid alkylation reactions for the reactants involved.

An additional object of this invention is to provide a method whereby the critical point of the reaction feed mixture is reduced by the addition of a material or materials having a critical temperature lower than that of the original isoparaffin/olefin reactants to which it is mixed.

A further object of this invention is to provide a method for the alkylation of an isoparaffin with an olefin under either supercritical fluid or near-supercritical fluid conditions, whereby the useful life of the catalyst is extended substantially because of the physical/chemical attributes of the supercritical or near-supercritical fluid systems.

These and other objects of the invention are addressed by a method for the alkylation of an isoparaffin with an olefin and a method of using a phase-modifying material in an isoparaffin olefin alkylation reaction. The method of the present invention comprising (a) forming a mixture of an isoparaffin, an olefin, and a phase-modifying material; (b) contacting the mixture with a solid acid catalyst member; and (c) applying a selectable temperature and a selectable pressure to the mixture whereby the mixture is either a near supercritical fluid or, a supercritical fluid such that the reaction temperature is from 0.75 to 1.2 times $T_c$ and reaction pressure is from 0.25 to 10 times $P_c$ relative to the reaction mixture. The phase-modifying material is a material that becomes supercritical at a temperature lower than the critical temperature of the isoparaffin and the olefin reactants. More specifically, the phase-modifying material is preferably selected from the group consisting of methane, ethane, propane, carbon dioxide, fluoromethane, trifluoromethane, sulfur hexafluoride, xenon, argon, hydrogen, nitrogen, and mixtures thereof.

DETAILED DESCRIPTION

The present invention includes a process for alkylating an olefin with an isoparaffin comprising (1) contacting an isoparaffin-containing feed with an olefin-containing feed with a solid catalyst material under alkylation conversion conditions, (2) including the presence of an additional component that facilitates the generation of either a supercritical fluid state, or a near-supercritical fluid state at temperatures that are lower than those used in other alkylation reactions that use supercritical fluids, (3) operating the reaction at temperatures between approximately 25% below to 20% above the critical temperature of the reaction feed mixture (on an absolute temperature scale), and (4) operating the reaction at pressures between approximately 75% below to 10 times above the critical pressure of the reaction feed mixture.

The use of ethane, for example, allows for a lower reaction temperature while maintaining the reaction system in either a supercritical fluid or a near-supercritical fluid state. The addition of one or more phase-modifying materials facilitates the change of state to either a supercritical or a near-supercritical fluid reaction system. That phase-modifying material causes the new reaction mixture to behave as either a supercritical fluid or a near-supercritical fluid at temperatures that are lower than the critical temperatures of the isoparaffin/olefin reactants. Thus, the benefits of supercritical fluid reaction conditions, as taught in the '698 patent, are achieved with the current invention at much lower temperatures than those previously required. Additionally, the current invention describes near-supercritical reaction conditions that are even more beneficial for the given reaction than supercritical fluid process conditions previously reported.

However, the practice of this invention is not limited to the use of ethane as the sole phase-modifying material. Indeed, many substances can be added that will provide the desired benefit of achieving a reaction that occurs within either a supercritical fluid or a near-supercritical fluid system. Benefits of either a supercritical fluid or a near-supercritical fluid reaction system are comprised of, but not limited to, the removal of side reaction waste or coke from the catalyst, enhanced desorption of the product from the catalyst, decreased temperature of reaction, increased efficiency of the catalyst, and increased efficiency of conversion from reactants to product. Additional materials may be used in the practice of this invention without limiting the scope of this invention, which is only limited by the attached claims.

Catalysts

This invention includes the group of useful catalysts including porous crystalline solids, layered materials, porous amorphous solids and nonporous solids. The non-zeolitic inorganic oxides of the solid catalyst may be selected from the diverse group comprising inorganic oxides, such as alumina, zirconium dioxide, chromia, zinc oxide, magnesia, calcium oxide, silica-alumina, silica-magnesia, silica-alumina-magnesia, silica-alumina-zirconia, sulfated nickel titania, sulfated zirconia, sulfated platinated zirconia, sulfated zirconium-aluminum, sulfated zirconium silicates, sulfated zirconia silanes, sulfated zirconia iron manganate, sulfated zirconia tungstenate, sulfated zirconia boronate, sulfated zirconia phosphorous, sulfated zirconia niobiomate, and the naturally occurring inorganic oxides of various states of purity, such as bauxite, clay and diatomaceous earth, just to name a few. The present invention further includes the use of zeolitic catalysts, such as HY, USY, CeY, LaY, BF3/USY, ZSM-5, Beta-zeolite, Pt/USY and mordenite and heteropolyacids.

Feedstocks

Feedstocks useful in practicing the present invention include at least one isoparaffin and at least one olefin and a suitable amount of a phase-modifying material or materials. The isoparaffin contains from about 4 to about 8 carbon atoms. Representative examples include isobutane, isopentane, 3-methylhexane, 2-methylhexane, 2,3-dimethylbutane, 2,4-dimethylhexane, and other analogues, which one of ordinary skill in the art would see as chemically similar. The olefin component of the feedstock includes at least one olefin having from 2 to 12 carbon atoms. Representative examples include 2-butene, 1-butene, isobutylene, propylene, ethylene, hexene, octene, heptene, and homologues, which one skilled in the art would see as chemically 6 analogous.

The weight percentage of the phase modifying material in the feedstock can range from about 5% to about 99% preferably in the range of 20% to 85%. Of course, a phase modifying material can be admixed with either the olefin or the isoparaffin feedstocks prior to combining the reactants and their addition to the reaction chamber. In other situations it may be desirable to admixed the phase-modifying material with only one of either the olefin or the isoparaffin feedstock prior to reaction. Accordingly, the weight percentage of phase-modifying material premixed with the olefin feedstock can range from 0% to 99%. Likewise the weight percentage of the phase-modifying material premixed with the isoparaffin feedstock can range from 0% to 99%. The phase-modifying material needs to be present in an amount suitable to solvate the reactants, reduce the reaction mixture's critical temperature, and facilitate the alkylation reaction.

Process Conditions

The alkylation process disclosed herein is suitably conducted at temperatures from about −20° C. to 140° C., preferably between about 25% below to about 20% above the critical temperature of the reaction mixture (on an absolute temperature scale). Concurrently, reaction pressure is suitably in the range of 250 psi to 5000 psi, preferably between 75% below to 10 times above the critical pressure of the reaction mixture. Importantly, both the judicious selection of the percent content of the phase modifying material within the reactant feed stream and the judicious selection of the reaction temperature and pressure will ensure the maintenance of either a supercritical fluid or a near-supercritical fluid reaction condition over the catalyst.

A "supercritical fluid" is a substance that presents many of the characteristics of both a gas and a liquid. Some of the displayed characteristics include, but are not limited to, density, expandability, contractibility, volume decrease upon the action of an applied exterior pressure, fluidity and molecular packing, viscosity and diffusivity. Moreover, a supercritical fluid is typically formed through the application of sufficient temperature up to a specific temperature above which, regardless of the amount of pressure applied, the material cannot be compressed into its liquid form. Thus, the last temperature at which the gas-to-liquid phase conversion can be made is termed the "critical temperature". A material heated above its critical temperature resides in a phase of matter termed the supercritical fluid phase. "Critical pressure" is defined as the minimum pressure required to perform the gas-to-liquid phase conversion of a material held at its critical temperature.

Importantly, however, the subject substance will begin to manifest many of the physical traits of a supercritical fluid before conditions actually cause the change of state of matter. This phenomenon is analogous to other changes in states of matter, such as when water is heated to the boiling point. Just prior to the water reaching the temperature at which it boils, it behaves similarly to the steam it will become in terms of molecular kinetics, energy, and, of course, temperature. Just prior to a liquid or gas becoming a supercritical fluid, it also begins to manifest some of the physical properties and attributes, such as density, viscosity, diffusivity and solubility, of the supercritical fluid it will become. Therefore, for the purposes of this document, when the reaction mixture is either at or below the critical temperature of the reaction mixture and the properties of the mixture begin to approach those of a supercritical fluid, the mixture is given the label of being a "near-supercritical fluid." For the purposes of this document, "near-supercritical fluid reaction conditions" include those conditions where the reaction is conducted at temperatures from about 75% of the critical temperature of the reaction mixture to about 100% of the critical temperature of the reaction mixture, and pressures from about 25% of the critical pressure of the reaction mixture to about 10 times the critical pressure of the reaction mixture.

"Near-supercritical fluids," for the purposes of this document, are further subdivided into two distinct categories of "near-supercritical gas and "near-supercritical liquid phases." The "near-supercritical gas phase" is defined as the phase that exists at temperatures either less than or equal to the critical temperature with pressures less than the bubble point pressure of the material or mixture of materials. The "near-supercritical liquid phase" is defined as the phase that exists at temperatures either less than or equal to the critical temperature and pressures either greater than or equal to the bubble point pressure of the material or mixture of materials. The purpose for making these phase distinctions will be made clear in the following Examples and their Conclusions.

Furthermore, for the purposes of this document, "supercritical fluid reaction conditions" are defined as those conditions where the reaction temperatures are greater than the critical temperature of the reaction mixture. For the purposes of this document, the preferred supercritical fluid reaction conditions includes reaction pressures from about 25% of the critical pressure of the reaction mixture to about 10 times the critical pressure of the reaction mixture while being at temperatures greater than about 1.0 times the critical temperature of the reaction mixture to temperatures equal to about 1.2 times the critical temperature of the reaction mixture.

Finally, for the purposes of this document, the "reaction feed mixture" is described as being comprised of at least one isoparaffin, one olefin, and one phase-modifying material.

The following examples set forth the preferred embodiments and techniques for practicing the present invention, as well as test results demonstrating effectiveness. It is to be understood, however, that these examples are presented by way of illustration only and nothing therein shall be taken as a limitation upon the overall scope of the invention.

EXAMPLES

Examples 1–3 show the estimated critical temperature and pressure for a reaction mixture of isobutane and trans-2-butene with a solvent. The critical constants were estimated using the Peng-Robinson equation of state. The ratio of isobutane to trans-2-butene in the reaction mixtures is 60:1. Table 1 lists the critical constants for the pure compounds.

TABLE 1

Critical Constants of Selected Compounds

| Compound | Critical Constants | |
|---|---|---|
| | Temperature (° C.) | Pressure (psia) |
| Methane | −82 | 667 |
| Ethane | 32 | 708 |
| Carbon Dioxide | 31 | 1070 |
| Isobutane | 135 | 529 |
| trans-2-butene | 156 | 600 |

Example 1

In this example, isobutane and trans-2-butene are mixed with methane. The estimated critical constants are shown in Table 2.

TABLE 2

Critical Constants for Mixtures with Methane

| Mole Fraction Methane | Critical Constants | |
|---|---|---|
| | Temperature (° C.) | Pressure (psia) |
| 0.4 | 102 | 1120 |
| 0.55 | 78 | 1430 |
| 0.7 | 41 | 1750 |
| 0.8 | 7 | 1800 |
| 0.85 | −18 | 1660 |

Example 2

In this example, isobutane and trans-2-butene are mixed with ethane. The estimated critical constants are shown in Table 3.

TABLE 3

Critical Constants for Mixtures with Ethane

| Mole Fraction Ethane | Critical Constants | |
|---|---|---|
| | Temperature (° C.) | Pressure (psia) |
| 0.7 | 78 | 790 |
| 0.9 | 51 | 770 |

Example 3

In this example, isobutane and trans-2-butene are mixed with carbon dioxide. The estimated critical constants are shown in Table 4.

TABLE 4

Critical Constants for Mixtures with Carbon Dioxide

| Mole Fraction $CO_2$ | Estimated Critical Constants | |
|---|---|---|
| | Temperature (° C.) | Pressure (psia) |
| 0.7 | 67 | 1065 |
| 0.9 | 38 | 1020 |

Examples 4–6 show isoparaffin-olefin alkylation over a USY zeolite catalyst. These experiments evaluated the effects that reduction of the reaction temperature have on product quality and yield. These experiments were operated at either supercritical fluid or near-supercritical liquid conditions. The critical temperature of the system was reduced by adding a phase-modifying material into the reaction mixture.

Examples 4–6 show that as the reaction temperature is lowered, while maintaining either a supercritical fluid or a near-supercritical liquid state, the product yield and quality are improved. As the temperature is decreased from 150° C., to 90° C., and then to 60° C., the trimethylpentane (TMP) yield increases from 20 Wt % to 50 Wt %, and then to 66 Wt %, respectively. Additionally, as the temperature is decreased from 150° C., to 90° C., and then to 60° C., the desired TMP product ratio increases from 1 to 2 to 4.7, respectively. This lowering of reaction temperature, while still maintaining a single, homogeneous reaction mixture phase, is accomplished through the addition of a phase-modifying material.

The following experiments were performed in a fixed-bed reactor. The USY zeolite catalyst was initially activated at 600° C., in air for three hours. Typically 1 gram of activated catalyst was loaded into the reactor and the catalyst heated overnight at 180° C., in flowing helium. Following the catalyst pretreatment, the reactor was cooled to the reaction temperature. The reactor was filled with the reaction mixture without olefin. The system pressure was brought up to the experimental pressure. The olefin-free mixture was then pumped through the reactor at the experimental flow rate. After approximately 15 minutes on-line the feed was switched to a reaction mixture that included the olefin. Catalyst time-on-line was measured from the point when the olefin containing feed started flowing to the reactor. All experiments took place at a weight hour space velocity (WHSV) of approximately 0.1 gram olefin/gram catalyst/ hour; and a feed isoparaffin to olefin ratio of 60:1. The isoparaffin used was isobutane and the olefin was trans-2-butene.

The reactor effluent, still at pressure, flowed through a high-pressure liquid sample valve through which a sample was introduced into a gas chromatograph (GC). The analysis by GC was used to determine conversion and selectivity.

Example 4

This example shows the effect of operating the catalytic reaction at supercritical conditions, above the critical temperature of the isobutane reactant, but without the addition of a phase modifying material. In this example, the reaction took place at a temperature of 150° C., and a pressure of 700 psig, above the critical temperature of isobutane ($T_c=135°$ C., $P_c=529$ psia).

Table 5 shows the initial and end-of-run product yields and selectivity. Table 5 shows that the TMP yield, as a percent of trans-2–16 butene in the feed, is relatively low, approximately 20 Wt %. Additionally, the TMP/dimethyl hexane (DMH) product ratio at 150° C. is low, less than 1.

TABLE 5

Initial and End-of-Run Product Yields
150° C., 700 psig SCF Conditions

|  | Initial (0.75 hrs) | End-of-Run (2.25 hrs) |
|---|---|---|
| $C_4^-$ Conv. (Wt %) | 100 | 100 |
| $C_{5+}$ Yield (gram/gram $C_4^-$ Conv.) | 1.63 | 0.98 |
| $C_{5+}$ Analysis: (Wt %) |  |  |
| $C_5$–$C_7$ | 65 | 45 |
| Total $C_8$ | 35 | 55 |
| TMP | 12.4 | 19.4 |
| TMP/DMH | .97 | .89 |

Example 5

This example shows the effect of adding a phase-modifying material to the reaction mixture, such that the critical temperature of the resulting mixture is lowered. In this example, 55 mole % methane is added to the isobutane/trans-2-butene reactants. The reaction took place at a pressure of 2030 psig and a temperature of 90° C.; thus, the reaction conditions were above the critical point of the mixture as shown in Example 1 ($T_c=78°$ C., $P_c=1430$ psia).

Table 6 shows the initial and end-of-run product yields and selectivity. Table 6 shows that the TMP yield, as a percent of trans-2-butene in the feed, is increased at lower temperatures, approximately 29 Wt % initially, increasing to nearly 50 Wt %. Additionally, the TMP/DMH product ratio at 90° C., is improved, starting at 1.4 initially, and increasing to 2.0.

TABLE 6

Initial and End-of-Run Product Yields
90° C., 2030 psig SCF Conditions

|  | Initial (0.75 hrs) | End-of-Run (2.25 hrs) |
|---|---|---|
| $C_4^-$ Conv. (Wt %) | 100 | 100 |
| $C_{5+}$ Yield (gram/gram $C_4^-$ Conv.) | 1.46 | 1.52 |
| $C_{5+}$ Analysis: (Wt %) |  |  |
| $C_5$–$C_7$ | 61 | 54 |
| Total $C_8$ | 39 | 46 |
| TMP | 19.9 | 32.3 |
| TMP/DMH | 1.4 | 2.0 |

Example 6

This example shows the effect of reducing the temperature further by adding a phase-modifying material to the reaction mixture. In this example, 70 mole % ethane was added to the isobutane/trans-2-butene reactants. The reaction took place at a pressure of 1200 psig and a temperature of 60° C. Thus, the reaction conditions were near-supercritical liquid, with a reaction temperature 18° C., below the critical point of the mixture, but at a pressure above the critical pressure of the mixture, as shown in Example 2 ($T_c=78°$ C., $P_c=790$ psia).

Table 7 shows the initial and end-of-run product yields and selectivity. Table 7 shows that the TMP yield, as a percent of trans-2-butene in the feed, is increased as temperature is still lowered, approximately 66 Wt % initially. Additionally, the TMP/DMH product ratio at 60° C., is significantly improved, starting at 4.7 initially, and undefined at the end-of-run since the entire $C_8$ product is TMP.

TABLE 7

Initial and End-of-Run Product Yields
60° C., 1200 psig SCF Conditions

|  | Initial (0.75 hrs) | End-of-Run (2.25 hrs) |
|---|---|---|
| $C_4^-$ Conv. (Wt %) | 100 | 100 |
| $C_{5+}$ Yield (gram/gram $C_4^-$ Conv.) | 1.29 | 0.71 |
| $C_{5+}$ Analysis: (Wt %) |  |  |
| $C_5$–$C_7$ | 38 | 32 |
| Total $C_8$ | 62 | 68 |
| TMP | 51.5 | 68.3 |
| TMP/DMH | 4.7 | — |

Conclusions for Examples 4–6

Examples 4–6 clearly show that product yield and selectivity are improved as the reaction temperature is lowered. Additionally, the addition of a phase-modifying material allowed for the reaction to take place in either a supercritical fluid, or a near-supercritical fluid phase at temperatures lower than could otherwise be achieved. Finally, these examples demonstrate that near-supercritical liquid phase conditions can result in improved product yield and selectivity over the supercritical fluid conditions.

Examples 7–10 show isoparaffin-olefin alkylation over a sulfated mixed oxide of titanium/nickel as described in U.S. Pat. No. 5,345,028. These experiments evaluated the effect of adding a phase-modifying material into the reaction mixture such that the reaction mixture phase was changed from a liquid to a supercritical fluid state. The supercritical fluid experiments were carried out at a temperature and pressure above the critical point of the system.

These experiments show that the catalyst deactivation rates in the supercritical fluid phase were much lower than at liquid phase conditions. The decline in trimethylpentane (TMP) yield from the initial sample to the end-of-run sample was as much as 21 times lower at supercritical fluid (SCF) conditions compared to liquid conditions. The end-of-run TMP yield was as much as 5-fold higher at SCF conditions compared to liquid conditions. SCF phase operation resulted in a 5-fold increase in product selectivity, and a four-fold increase in $C_{5+}$ yield, as a fraction of butene conversion, at the end-of-run.

The following experiments were performed in a fixed-bed reactor. Typically 2 grams of catalyst was loaded into the reactor and the catalyst was heated for three hours at 360° C., in flowing helium. Following the catalyst pretreatment, the reactor was cooled to the reaction temperature. The reactor was filled with the reaction mixture without the olefin. The system pressure was brought up to the experimental pressure. The olefin-free reaction mixture was then pumped through the reactor at the experimental flow rate. After approximately 15 minutes on-line the feed was switched to a reaction mixture that included the olefin. Catalyst time-on-line was measured from the point when the olefin containing feed started flowing to the reactor. All experiments took place at a temperature of 90° C.; a weight hourly space velocity (WHSV) of approximately 0.1 gram olefin/gram catalyst/hour; and a feed isoparaffin to olefin ratio of 60:1. The isoparaffin used was isobutane and the olefin was trans-2-butene. The experiment was run for two hours.

The reactor effluent flowed across a valve where the pressure dropped to atmospheric. A sample of the reactor effluent at atmospheric pressure was collected in a gas sample bag. The collected sample was analyzed by gas chromatography using an internal standard to determine conversion and selectivity. The first sample in each experiment was taken after 20 minutes on-line, and the last sample was taken at 2 hours on line.

Example 7

This example shows the effect of operating the catalytic reaction in a liquid phase without the addition of a phase-modifying material. In this example, the reaction took place at a pressure of 600 psig. The temperature of the reaction was 90° C., well below the critical temperature of isobutane and trans-2-butene ($T_c$=135° C., and $T_c$=156° C., respectively).

Table 8 shows the initial (20 minutes on-line) and end-of-run (2 hours on-line) product yields and selectivity. Table 8 shows that butene conversion declines to 49% of its initial value in 100 minutes while the TMP yield drops 46 fold in the 100 minutes between samples.

TABLE 8

Initial and End-of-Run Product Yields
Liquid Phase Conditions

|  | Initial (20 minutes) | End-of-Run (2 hours) |
|---|---|---|
| $C_4^-$ Conv. (Wt %) | 100.0 | 48.7 |
| $C_{5+}$ Yield (gram/gram $C_4^-$ Conv.) | 0.42 | 0.41 |
| $C_{5+}$ Analysis: (Wt %) |  |  |
| $C_5$–$C_7$ | 33 | 6 |

TABLE 8-continued

Initial and End-of-Run Product Yields
Liquid Phase Conditions

|  | Initial (20 minutes) | End-of-Run (2 hours) |
|---|---|---|
| Total $C_8$ | 54 | 87 |
| Total $C_{9+}$ | 13 | 7 |
| TMP | 30 | 1.4 |
| TMP/DMH | 2.0 | 0.10 |

Example 8

This example shows the effect of adding a phase-modifying material to the reaction mixture such that the catalytic reaction occurs in a supercritial phase. In this example, 70 mole % ethane was added to the isobutane/trans-2-butene reactants. The reaction took place at a pressure of 1200 psig and at a temperature of 90 ° C.; thus, the reaction conditions were above the critical point of the mixture as shown in Example 2 ($T_c$=78° C., $P_c$=790 psig).

Table 9 shows the initial (20 minutes on-line) and end-of-run (2 hours on-line) product yields and selectivity. Table 9 shows that the TMP yield drops only 2 fold in the 100 minutes between samples, whereas the liquid phase operation showed a 46 fold decline in the TMP yield. The TMP yield was approximately 3 fold higher in the supercritical fluid phase experiment at the end-of-run. Additionally, the $C_{5+}$ yield, as a fraction of butene conversion, was approximately 4 fold higher at the end-of-run in the supercritical phase operation as compared to the liquid phase operation.

TABLE 9

Initial and End-of-Run Product Yields
Supercritical Fluid Conditions, 1200 psig

|  | Initial (20 minutes) | End-of-Run (2 hours) |
|---|---|---|
| $C_4^-$ Conv. (Wt %) | 35.8 | 10.3 |
| $C_{5+}$ Yield (gram/gram $C_4^-$ Conv.) | 0.79 | 1.64 |
| $C_{5+}$ Analysis: (Wt %) |  |  |
| $C_5$–$C_7$ | 22 | 13 |
| Total $C_8$ | 39 | 56 |
| Total $C_{9+}$ | 39 | 31 |
| TMP | 6.3 | 4.9 |
| TMP/DMH | 1.1 | 0.80 |

Example 9

This example shows the effect of adding a phase-modifying material to the reaction mixture such that the catalytic reaction occurs in a supercritical phase at 2500 psig. In this example, 70 mole % ethane was added to the isobutane/trans-2-butene reactants. The reaction took place at a pressure of 2500 psig and at a temperature of 90° C., such that the pressure and temperature were above the critical point of the mixture.

Table 10 shows the initial (20 minutes on-line) and end-of-run (2 hours on-line) product yields and selectivity. In this experiment, the TMP yield was approximately 5 fold higher in the supercritical fluid phase experiment at the end-of-run as compared to the liquid phase experiment.

TABLE 10

Initial and End of-Run Product Yields
Supercritical Fluid Conditions, 2500 psig

| | Initial (20 minutes) | End-of-Run (2 hours) |
|---|---|---|
| $C_4^=$ Conv. (Wt %) | 77.2 | 34.5 |
| $C_{5+}$ Yield (gram/gram $C_4^=$ Conv.) | 0.52 | 0.80 |
| $C_{5+}$ Analysis: (Wt %) | | |
| $C_5$–$C_7$ | 27 | 16 |
| Total $C_8$ | 34 | 58 |
| Total $C_{9+}$ | 39 | 26 |
| TMP | 9.0 | 4.9 |
| TMP/DMH | 1.1 | 0.74 |

Example 10

This example shows the effect of adding a phase-modifying material to the reaction mixture such that the catalytic reaction occurs in a supercritical phase at 4000 psig. In this example, 70 mole % ethane was added to the isobutane/trans-2-butene reactants. The reaction took place at a pressure of 4000 psig and at a temperature of 90° C.; thus, the reaction conditions were above the critical point of the mixture.

Table 11 shows the initial (20 minutes on-line) and end-of-run (2 hours on-line) product yields and selectivity. In this experiment, the TMP yield was approximately 5 fold higher in the supercritical fluid phase experiment at the end-of-run as compared to the liquid phase experiment. The product selectivity, as measured by the TMP/DMH ratio was nearly 9-fold higher in the supercritical fluid phase experiment as compared to the liquid phase experiment.

TABLE 11

Initial and End-of-Run Product Yields
Supercritical Fluid Conditions, 1200 psig

| | Initial (20 minutes) | End-of-Run (2 hours) |
|---|---|---|
| $C_4^=$ Conv. (Wt %) | 67.5 | 29.0 |
| $C_{5+}$ Yield (gram/gram $C_4^=$ Conv.) | 0.63 | 0.72 |
| $C_{5+}$ Analysis: (Wt %) | | |
| $C_5$–$C_7$ | 29 | 19 |
| Total $C_8$ | 43 | 69 |
| Total $C_{9+}$ | 28 | 12 |
| TMP | 11.7 | 6.4 |
| TMP/DMH | 0.94 | 0.88 |

Conclusions for Examples 7–10

Examples 7–10 demonstrate that supercritical fluid phase operation reduces catalyst deactivation over liquid phase operation. Additionally, modifications in pressure can result in variations in catalyst lifetimes as well as product yield and selectivity.

We claim:

1. A method for alkylation of an isoparaffin with an olefin comprising reacting an isoparaffin and an olefin in the presence of a solid acid catalyst member and a phase-modifying material that substantially lowers the temperature at which the reaction takes place, under alkylation conversion and at near-supercritical liquid phase conditions, wherein the reaction mixture is in a liquid state having a temperature of less than or equal to the critical temperature and a pressure greater than or equal to the bubble point pressure of the reaction mixture.

2. The method of claim 1 wherein the phase-modifying material is a material that becomes supercritical at a temperature lower than the critical temperature of the isoparaffin and the olefin reactants.

3. The method of claim 2 wherein the phase-modifying material is selected from the group consisting of methane, ethane, propane, carbon dioxide, fluoromethane, trifluoromethane, sulfur hexafluoride, xenon, argon, hydrogen, nitrogen and mixtures thereof.

4. The method of claim 1 where the isoparaffin is predominately isobutane and the olefin is predominately butene, the isoparaffin to olefin ratio is from 1:1 to 100:1, and preferably from 5:1 to 60:1.

5. The method of claim 1 wherein the catalyst member is selected from the group consisting of porous crystalline solids, layered materials, porous amorphous solids, nonporous solids, inorganic oxides, sulfated metal oxides, alumina, zirconium dioxide, chromia, zinc oxide, magnesia, calcium oxide, silica-alumina, silica-magnesia, silica-alumina-magnesia, silica-alumina-zirconia, sulfated nickel titania, sulfated zirconia, sulfated platinated zirconia, sulfated zirconium-aluminum, sulfated zirconium silicates, sulfated zirconia silanes, sulfated zirconiairon manganate, sulfated zirconia tungstenate, sulfated zirconia boronate, sulfated zirconia phosphourous, sulfated zirconia niobiomate, bauxite, clay, diatomaceous earth, HY, USY, CeY, LaY, BF3/USY, ZSM-5, Beta-zeolite, PtUSY, mordenite, alumina, zirconium dioxide, chromia, zinc oxide, magnesia, calcium oxide, heteropolyacids and mixtures thereof.

6. The method of claim 1 where the phase modifying material is methane, the molar composition of methane in the system is between 5% and 90%, preferably between 20% and 65%, the reaction temperature is between –15° C., and 140° C., the pressure is between 500 psia and 5000 psia, and the catalyst consists primarily of an USY zeolite or a sulfated metal oxide, including sulfated zirconia or sulfated titanium/nickel oxide mixtures.

7. The method of claim 1 where the phase-modifying material is ethane, the molar composition of ethane in the system is between 5% and 90%, preferably between 20% and 70%, the reaction temperature is between –15° C., and 140° C., the pressure is between 250 psia and 5000 psia, and the catalyst consists primarily of an USY zeolite or a sulfated metal oxide, including sulfated zirconia or sulfate titanium/nickel oxide mixtures.

8. The method of claim 1 where the phase modifying material is carbon dioxide, the molar composition of carbon dioxide in the system is between 5% and 90%, the reaction temperature is between –15° C., and 140° C., the pressure is between 250 psia and 5000 psia, and the catalyst consists primarily of an USY zeolite or a sulfated metal oxide mizture including, such as sulfated zirconia or sulfate titanium/nickel oxide.

9. The method of claim 1 where the phase modifying material is propane, the molar composition of propane in the system is between 5% and 90%, the reaction temperature is between –15° C., and 140° C., the pressure is between 250 psia and 5000 psia, and the catalyst consists primarily of an USY zeolite or a sulfated metal oxide mixtures, including sulfated zirconia or sulfate titanium/nickel oxide.

10. The method of claim 1 where the phase modifying material is trifluoromethane, the molar composition of trifluoromethane in the system is between 5% and 90%, the reaction temperature is between –15° C., and 140° C., the pressure is between 250 psia and 5000 psia, and the catalyst consists primarily of an USY zeolite or a sulfated metal oxide, including sulfated zirconia or sulfate titanium/nickel oxide mixtures.

11. A method of using a phase-modifying material in an isoparaffin olefin alkylation reaction comprising:
(a) forming a mixture of an isoparaffin, an olefin and a phase modifying material;
(b) contacting said mixture with a solid acid catalyst member; and
(c) applying a selectable temperature and a selectable pressure to said mixture whereby said mixture is a near-supercritical liquid phase and wherein the reaction mixture is in a liquid state having a temperature of less than or equal to the critical temperature and a pressure greater than or equal to the bubble point pressure of the reaction mixture.

12. The method of claim 11 wherein the phase-modifying material is a material that becomes supercritical at a temperature lower than the critical temperature of the isoparaffin and the olefin reactants.

13. The method of claim 12 wherein the phase-modifying material is selected from the group consisting of methane, ethane, propane, carbon dioxide, fluoromethane, trifluoromethane, sulfur hexafluoride, xenon, argon, hydrogen, nitrogen and mixtures thereof.

14. The method of claim 11 wherein the isoparaffin is predominantly isobutane and the olefin is predominantly butene.

15. The method of claim 11 wherein the catalyst member is selected from the group consisting of porous crystalline solids, layered materials, porous amorphous solids, nonporous solids, inorganic oxides, alumina, zirconium dioxide, chromia, zinc oxide, magnesia, calcium oxide, silica-alumina, silica-magnesia, silica-alumina-magnesia, silica-alumina-zirconia, sulfated nickel titania, sulfated zirconia, sulfated platinated zirconia, sulfated zirconium-aluminum, sulfated zirconium silicates, sulfated zirconia silanes, sulfated zirconiairon manganate, sulfated zirconia tungstenate, sulfated zirconia boronate, sulfated zirconia phosphourous, sulfated zirconia niobiomate, bauxite, clay, diatomaceous earth, HY, USY, CeY, LaY, BF3/USY, ZSM-5, Beta-zeolite, PtUSY, mordenite, alumina, zirconium dioxide, chromia, zinc oxide, magnesia, calcium oxide and mixtures thereof.

16. The method of claim 11 where the phase modifying material is methane, the molar composition of methane in the system is between 5% and 90%, preferably between 20% and 65%, the reaction temperature is between −15° C., and 140° C., the pressure is between 500 psia and 5000 psia, and the catalyst consists primarily of an USY zeolite or a sulfated metal oxide, including sulfated zirconia or sulfated titanium/nickel oxide mixtures.

17. The method of claim 11 where the phase-modifying material is ethane, the molar composition of ethane in the system is between 5% and 90%, preferably between 20% and 70%, the reaction temperature is between −15° C., and 140° C., the pressure is between 250 psia and 5000 psia, and the catalyst consists primarily of an USY zeolite or a sulfated metal oxide, including sulfated zirconia or sulfate titanium/nickel oxide mixtures.

18. The method of claim 11 where the phase modifying material is carbon dioxide, the molar composition of carbon dioxide in the system is between 5% and 90%, the reaction temperature is between −15° C., and 140° C., the pressure is between 250 psia and 5000 psia, and the catalyst consists primarily of an USY zeolite or a sulfated metal oxide mixture, including such as sulfated zirconia or sulfate titanium/nickel oxide.

19. The method of claim 11 where the phase modifying material is propane, the molar composition of propane in the system is between 5% and 90%, the reaction temperature is between −15° C., and 140° C., the pressure is between 250 psia and 5000 psia, and the catalyst consists primarily of an USY zeolite or a sulfated metal oxide mixtures, including sulfated zirconia or sulfate titanium/nickel oxide mixtures.

20. The method of claim 11 where the phase modifying material is trifluoromethane, the molar composition of trifluoromethane in the system is between 5% and 90%, the reaction temperature is between −15° C. and 140° C., the pressure is between 250 psia and 5000 psia, and the catalyst consists primarily of an USY zeolite or a sulfated metal oxide, including sulfated zirconia or sulfate titanium/nickel oxide mixtures.

* * * * *